United States Patent [19]

Othmer

[11] 4,017,421
[45] Apr. 12, 1977

[54] WET COMBUSTION PROCESS

[76] Inventor: Donald F. Othmer, 333 Jay St., Brooklyn, N.Y. 11201

[22] Filed: Dec. 16, 1975

[21] Appl. No.: 641,335

[52] U.S. Cl. .............................. 252/416; 423/659; 260/687 R; 260/346.1 R; 260/528; 159/1 RW; 159/47 WL; 162/31; 260/124 R; 423/42; 203/11; 203/12; 203/38; 203/73; 203/88

[51] Int. Cl.$^2$ ..................... B01D 15/06; B01D 1/14

[58] Field of Search .................. 203/10, 11, 12, 14, 203/28, 21, 22, 25, 27, 31, 38, 71, 74, 77, 76, 78, 80, 82, 84, 88, 91, 85, 92, 96, DIG. 20, DIG. 11, DIG. 17; 159/47 R, 47 WL, 1 RW; 423/659, 23, 42; 260/687 R, 209, 346.1, 528, 124; 162/30, 30 K, 31, 35, 70, 71, 91, 93; 252/411 R, 416, 419, 421, 445; 210/26, 63 R; 202/172, 173

[56] References Cited

UNITED STATES PATENTS

| 3,647,638 | 3/1972 | Osdor | 203/11 |
| 3,692,634 | 9/1972 | Othmer | 203/11 |
| 3,880,703 | 4/1975 | Hardman | 159/15 |

*Primary Examiner*—Hiram H. Bernstein

[57] ABSTRACT

Aqueous solutions and suspensions of solid particles, even those containing less than one percent of organic materials, may be combusted with air, oxygen, or their mixtures in a process which provides for preheating in countercurrent batches of the raw original liquid by either open (direct contact) or closed (heat transfer surface) condensation of steam generated by multiple flash evaporations which cool earlier batches of hot liquid after the wet combustion. Excess heat may often be withdrawn from the process for power generation or other use as high pressure steam, with or without combustion gases and other non-condensibles. No pumps are necessary, liquid batches are pressurized by steam generated in the flash evaporations for which only one pressure vessel is required instead of the many in the continuous processes.

Waste liquids as sewage sludges and black liquors from wood pulping may have their organic constituents, as measured by BOD or COD, so reduced that the final, spent liquid may be discharged directly to a receiving body of water.

40 Claims, 2 Drawing Figures

WET COMBUSTION PROCESS

There are various modifications of the process which is basically a batch preheating of a liquid to a desired high temperature at which a physical or chemical reaction takes place with an added material, and then a batch cooling of the liquid while giving up heat for the preheating of raw liquid. Thus there may be accomplished a wet revivification of activated carbons fully charged with impurities, also the partial wet combustion of many organics to give very simple intermediary products such as acetic acid or its alkaline salts and/or very complex molecules of materials, e.g. some related to lignin and having other industrial uses, also the hydrolysis of the cellulose in lignocellulose particles to give reducing sugars, furfural and acetic acid, with a residue of a lignin useable in plastics, etc. Still other reactions may be so operated which require additional prime or outside heat to raise the temperature above that of the preheating. Also physical operations may be advantageously conducted with the batch preheating and cooling of the liquid by the process and at the desired high temperature, e.g. the extraction of water from sea water by a solvent having a greater solubility for water hot than cold.

Wet combustion, or selective partial wet combustion of organic materials in solution or in particulate or powder form, may be conducted in a batch manner. Usually these materials to be processed are wastes or others of little value and are in an aqueous liquid solution and/or suspension or slurry containing 10 to 20 times as much water. Major advantages result from the use of this batch process compared with the continuous processes heretofore used. The combustion may be accomplished in the aqueous liquid by air, oxygen, or mixtures thereof. Similarly some other chemical reactions, such as the hydrolysis of organic materials, also some physical operations, as the extraction of water from an aqueous solution by another liquid, may be accomplished in the preferred batch manner to be described.

The process provides for the heating of batches of the raw aqueous liquid to be processed from a lower temperature, usually near the ambient, to a substantially higher temperature at which the action of some one or more materials added to the aqueous liquid accomplishes the change of the concentration of one or more of its constituents. After this chemical or physical processing, each batch of the aqueous liquid is cooled by individual and separate flash evaporations repeated by at least two or three times and as many times as may be practical, usually not more than 10 to 20. Successively lower temperatures and pressures are attained for the batch, finally approaching those of the original aqueous liquid. The spent cooled liquid, may have had substantially all of the organic constituents, or only a selected part of them removed by the combustion in such a process.

The several flash evaporations, while cooling the aqueous liquid from the maximum processing temperature, generate separate amounts of steam which are used countercurrently to heat, by their condensation — usually but not necessarily by direct and open condensation — successive batches of the original aqueous liquid. Finally, there is approached the high temperature necessary for the essential physical or chemical action which changes the concentration of at least some of the original constituents. In some cases an additional, prime heat source is used to heat to this desired high temperature, in other processes the heat of the reaction itself supplies all of the heat necessary - and sometimes much more, as in wet combustion.

One of the main uses of the process is to remove the large amount of organic material in waste liquors with their high BOD (biological oxygen demand) or high COD (chemical oxygen demand) as exemplified by raw sewage, sewage sludges, and black liquors from wood pulping operations. The wet combustion by removal of part or all of the oxidizable carbon thus reduces greatly, or almost completely, the BOD or COD in the spent liquid which then may often be discharged directly to the receiving body of water.

An earlier continuously operated system has been described in U.S. Pat. No. 3,692,634. Just such a change in concentration is accomplished in one or more constituents of the aqueous liquid. The heating of the aqueous liquid was by direct condensation of steam formed after the changes in concentrations during the cooling by successive flash evaporations. The system of multiflash evaporation with open condensation of the steam vapors formed on another liquid circulated in countercurrently operated stages has been called the Vapor Reheat method. One simple embodiment is the passing or sparging of the flash generated steam as bubbles through holes in a pipe - called a sparger - submerged in the batch of liquid.

However, in the process of U.S. Pat. No. 3,692,634 a pump was required to force the original aqueous liquid between each of the condensing-heating stages used in series to bring the liquid up to the highest temperature possible by this heat interchange system. Also in other similar processing, wherein the heat interchanging has been by standard tubular heat interchangers, rather than by flash evaporation and open condensation of vapors, there has been required a pump, often positive displacement, which has to force the liquid continuously throughout the entire pressure range from the lowest to the highest in the system — sometimes thousands of pounds per square inch, plus the friction head loss through the piping and heat exchangers.

Also, U.S. Pat. No. 3,692,634 showed that added heat over that recovered in the heat interchangers, and often called prime heat, could be supplied by the so-called and conventional submerged combustion of an added fluid fuel to give the maximum temperature necessary for the desired reaction. (Whether chemical or physical change is accomplished the single term reaction may be used, hereinafter.) This requires the careful balancing of the metering and supply of the amount of fuel as well as of the oxygen or air.

Now it has been found that not only may a submerged combustion be used as conventionally in the present invention as a source of prime heat, but a wet combustion may be accomplished to serve the same purpose by adding a water soluble fuel as methanol or other alcohol or a particulate fuel as sawdust to the liquid to be processed and operating as hereinafter described. However, in using wet combustion all of the liquid has to be heated to the very high temperature of the combustion, while with the use of submerged combustion as conventionally practiced only the liquid adjacent to the hot gases of the actual flame are so heated, and only to a much lower temperature than that of the hottest gases themselves.

The aqueous material processed in this invention may not be a flowable liquid as necessary with the continuous streams of prior processes. Some materials can be handled as liquids only after they have been treated with a substantial amount of water or heated substantially above the ambient; e.g., peat as it is dug in the bogs and containing 70 to 95% water, but still a nonpumpable, semi-solid mass. With the present process, in working with such material it may be charged as a batch from which it is not removed until it has been heated and processed into a flowable fluid. However, hereinafter the process liquid whether it is solution, slurry, or suspension of particles— may be referred to simply as the liquid, and this includes whatever materials may be dissolved or in suspension, usually to an extent of not more than 1/5th to 1/20th of the weight of the water, but sometimes less than 1%, as with raw sewage.

The present invention shows that the advantages of the previous continuous processes may be realized in a batch process with very much simpler, less expensive equipment, at a much lower cost of operation, and with much more flexibility of control, particularly for smaller or moderate sized plants. In particular, this new process largely eliminates the large pumping charges, both as to the costs of the pumps themselves and their operation and maintenance charges. There is required only the use of a simple transfer pump which will fill a vessel at atmospheric pressure with the cold, raw original liquid. Furthermore the handling of nonflowable material is greatly simplified; and the cost of handling a large amount of diluting water is eliminated.

In the continuous operation of U.S. Pat. No. 3,692,634 there were as many pressure chambers or vessels to accomplish the multiple flash evaporations as there were pressure chambers for the condensations. Using the improved batch system, only one pressure chamber or vessel is used for the multiple flash evaporations. This represents a considerable saving in equipment, particularly when a larger number of flash evaporations and condensations are used to improve the efficiency of the heat transfer operation.

Often the greatest advantage of the new process is the fact that, as explained hereinafter, its simplicity of equipment and operation may allow it to be used in installations which would be too small to justify the relatively expensive equipment, controls, and operation of the continuous processes of U.S. Pat. No. 3,692,634. Furthermore because of the repetitive and cyclic nature of the present operations, the process may be operated by automatic controls so as to minimize the cost of operating personnel.

This invention is concerned with aqueous solutions and/or suspensions. In most uses, the dissolved materials are not present in amounts which will significantly change the boiling point of the aqueous liquid from that of pure water; and therefore the vapors given off by flash evaporations may be regarded substantially as saturated vapors from water itself at the given temperature. In those cases, when there is a substantial elevation of boiling point of the aqueous solution, the effective condensing temperature of the vapors will be that of vapors from pure water, boiling at the particular pressure, i.e. the actual boiling point minus the elevation of boiling point. Thus, as always, there will be some loss in the available temperature range of the heat transfer operation when dealing with concentrated solutions. Since the invention and its operation is along the saturation, pressure-temperature line for water it is necessary — as is done usually hereinafter — to refer only to the temperature of the liquid at the particular point in the process because the pressure automatically follows from the vapor-pressure temperature curve for water. Often pressures may be subatmospheric.

Of much more concern in the important uses of the invention, there may be a large amount of non-condensible gases which may be formed as products of a wet combustion or other reaction. At the temperature developed in the liquid, these gases will give a very much higher supernatent pressure in the reactor itself than would be expected from the boiling or saturation temperature of pure water. It is possible usually to vent these gases to separate them substantially, from the relatively high pressure steam then generated in a first flash evaporation, so that this steam - over and above that required for the preheating operation - may be utilized for power generation. Subsequent flash evaporations are used for the preheating heat transfer operation. Sometimes most of these non-condensible gases from a wet combustion, with a substantial amount of steam, may be used directly in an expansion turbine or other engine to generate power before the flash evaporation is conducted to give nearly pure water vapors for use in preheating subsequent batches of raw liquid. At the subatmospheric pressures of the lower flash evaporations and condensations involved, suitable means for subatmospheric venting of non-condensible gases are provided.

BACKGROUND OF THE INVENTION

The process of wet combustion (or wet oxidation, as it is often called) was developed in Sweden by Cederquist in the late 1940's for processing peat, and by Zimmerman in the United States for processing sewage liquids and black liquors from the wood pulping industry. Patents were granted to both in the early 1950's; and both depended on tubular heat exchangers, high pressure pumps, and particularly on continuous processing and streams of liquids and gases to heat the aqueous liquors to the high temperatures necessary for the combustion to be ignited in the aqueous solution or slurry by the addition of air. Both also passed the hot liquid, after the wet combustion, to the heat exchangers for preheating the original liquid; and both used one or more high pressure pumps to raise the liquid to the maximum pressure of the reaction or combustion zone.

Othmer in U.S. Pat. No. 3,692,634 showed that the expensive and highly corrodable tubular heat exchangers could be replaced by the open condensation of steam, without heat transfer surfaces — the so-called Vapor Reheat system. This operates a series of stages of multiple flash evaporations of the hot liquid after the web combustion, each flash evaporating stage then supplying steam from its one of the successive multiple flash evaporations to a corresponding one of a multiplicity of open condensation stages in a counter current system. The original liquid was thus heated by the several condensations of steam — from the corresponding flash evaporations — to the high temperature appropriate and necessary for the process in question. In some cases, after the preheating operation it was necessary to heat in a prime heater still further with steam or other heat source to bring to the high temperature necessary for the chemical or physical process. In other cases e.g. wet combustion, the reaction itself supplied the heat necessary to make up — or even much more than make up — the heat losses in the heat interchanging system, thus no other source of prime heat was necessary.

While the flash evaporation of a liquid or of a batch of liquid is often referred to, it is to be noted that actually only a relatively small amount of the liquid is actually converted to steam. Thus a liquid at the temperature of 250° F and a corresponding pressure may have the pressure above it lessened so that it flash evaporates as it generates steam to help it come to equilibrium with the new pressure. If the controlling temperature is that of open condensing water which establishes a temperature of, say 225° F, and corresponding pressure, then the hot liquid may be cooled a maximum of 250°–225° or 25°. Since the specific heat of water is approximately 1 BTU per pound per °F and the latent heat per pound is roughly 1000 BTU per pound, it follows that about 25/1000 or 0.025 pounds of steam will be generated for every pound of water cooled in this single flash evaporation. Also if the same amount of water (1 pound) was being heated by this condensation, the 25 BTU input would have raised that water 25° F; and its original temperature must have been 225°–25° = 200° F. Many corrections would be needed to refine this simple heat balance, but it is illustrative for the purpose.

Also U.S. Pat. No. 3,692,634 showed that a wet combustion could be controlled so as to oxidize some compound or class of organic compounds which were "softer" or relatively easily oxidized while not oxidizing others which are "harder" or more difficult to oxidize. This is referred to as a partial oxidation or a partial combustion.

U.S. Pat. No. 3,692,634 described other processes, involving physical and/or chemical operations at high temperatures with aqueous liquids — solutions and/or slurries — which can be accomplished using Vapor Reheat heat exchanging which is operated continuously. This heat exchange system with heat transfer surfaces heats the cold liquid and its accompanying solid constituents - either dissolved or suspended - and cools the hot liquid. However, U.S. Pat. No. 3,692,634 requires pumps operating between the condensing side of each of the condensing stages to pump the liquid to the higher pressure of the next higher stage. These pumps taken together bring the liquid to the highest pressure in the system. Again there is the capital expense of the pumps and the expense of their operation and maintenance.

The process of U.S. Pat. No. 3,692,634 demonstrated that it could be used for the hydrolysis of carbohydrate materials, also the wet combustion of sewage liquids, and of black liquors from wood pulping operations. With simultaneous treatment with an alkaline material as sodium or calcium carbonate or calcium hydroxide, the wet combustion gave alkaline acetates. The production and revivification of powdered activated carbons was also disclosed, also the extraction of water from sea water with solvents having different mutual solubilities at higher and lower temperatures, and other processes wherein a physical operation or a chemical reaction takes place at an elevated temperature due to the addition of another material. The present improvement operating with batches of liquid allows the accomplishment of each of these processes with additional advantages when operated as described hereinafter.

The novel advantages of this new batch process also are noted in those cases where, for particular reasons, it may be desired to accomplish the condensation of the vapors of this batch heat transfer operation in a closed condensing system. This will produce distilled water, will allow a more concentrated liquid for the reaction and will produce a higher concentration in the effluent or spent liquor. This may be particularly valuable with those processes operating over a large temperature range, e.g. wet combustion because of the large amount of steam formed in the several flash evaporations, with corresponding losses of liquid and changes in its concentration, and of the large amount of distilled water which can be produced.

Particularly in those cases where a desired chemical reaction is to be completed, the present batch process allows a precise control which is difficult or impossible with the continuous processes. Thus, in the partial wet combustion in the presence of an alkali of organic materials, as sewage sludges and wood pulping black liquors, the concentration of acetate salts increases. This is because acetic acid is formed as an intermediate product in the partial wet combustion of many organic materials. At the maximum concentration, the wet combustion can be stopped, the liquors are removed and treated with sulfuric acid to give free acetic acid; and this can be recovered, by known methods, e.g. those of U.S. Pat. No. 2,878,283.

The wet combustion of carbohydrate material — i.e. sugars, starches, celluloses, etc. — gives acetic acid as such as one of the intermediary products, and it may be removed in a dilute form from surface condensers in the preheating vessels; or if alkali is present, as the alkaline acetate. In either case it may ultimately be recovered as glacial acetic acid by known processes. The intermediary steps in the breakdown and oxidation of the large carbohydrate molecule may only be surmised, one sequence may be via alcohol, then aldehyde, as in the chemistry of other processes. Ethanol itself in a wet oxidation in aqueous solution has been found to give acetic acid as such or as an acetate salt in the presence of an alkali.

In other treatments by partial wet combustion by this method, of waste liquids such as those from the pulp industry, the addition of oxides, hydroxides, or carbonates of calcium, magnesium, or iron, results in insoluble salts or complexes of acids of higher molecular weights than acetic acid; and by stopping of the wet combustion short of burning out the carbon and hydrogen of these salts or complexes, and filtering them out of the spent liquors, water insoluble materials of value may be obtained. These materials are difficult or almost impossible of analysis but may be used as a cheap extender of asphalts in many of their uses.

Before, during and/or after the processing of a batch, the vessel it is in may have to be vented. If at a superatmospheric pressure non-condensible gases may generate power or go to the atmosphere, if at lower pressures, means for subatmospheric venting through a corresponding vacuum are provided.

AIMS AND ACCOMPLISHMENTS

It is thus possible through the operation of the present method to accomplish by batch processing: (a) the heating of an aqueous liquid (including solutions and/or slurries) to a relatively high temperature, (b) the chemical or physical change of the concentrations of the components of the aqueous liquid at the high temperature through contact with some other material which is added to the liquid, (c) the cooling of the liquid after the chemical or physical change by several or more successive flash evaporations, whereby the original aqueous liquid is heated countercurrently by the condensation of the individual vapors from the several flash evaporations.

All of these operations are conducted without pumps and often without heat exchange surfaces, and in simple equipment, only approximately one half as many heat exchange chambers or vessels are required as by the previous continuous processes.

Also various chemical materials may be produced by the basic steps of hydrolysis and/or wet combustion from such cheap materials as sawdust, or indeed from waste liquors as sewage or pulping liquors. These chemicals may include very simple ones as acetic acid and furfural, or very complex ones of unidentified molecular structures as lignin residues or metallic complexes of ligno sulfonic or other acids of high molecular weight.

EXAMPLES OF BATCH SEQUENCES

There are numerous methods by which a sequence of batch operations may be used to accomplish the invention, and only two will be indicated. Each sequence allows the operation without any pump to elevate the liquid to the high temperature and pressure of the reaction; and one will also allow the handling of quite unpumpable mixtures of solids or semi-solids and liquid through the series of preheating, reaction, and flash evaporations. The time of the reactions for which this process may be used is between 1 and 200 minutes, so the sequences are designed with adequate time between the preheating and cooling operations.

In both these sequences, there are required — due to the advantage of the batch operation of the process — substantially only the number of heat transfer vessels as total stages of the heat transfer — say for five stages, five heat transfer vessels plus one evaporation vessel. On the other hand, always in the continuous process — when using either the usually preferred direct and open condensation of the Vapor Reheat method or the closed condensers for preheating — there have been required more heat transfer vessels, i.e. for five stages there would be five flash evaporative vessels and five condensation vessels. The same advantage holds with this batch process when it uses an indirect heat transfer to save condensate and to increase the concentration of the spent liquid. In both cases this is because all of the flash evaporations are conducted batch-wise from a single vessel rather than from the same number of evaporating as condensing vessels of the continuous processes.

Sequence A.

Consider a batch sequence of the process indicated with a given batch of the liquid remaining in a vessel used as the Reactor after the physical operation or the chemical reaction, at the highest temperature in the system. After the reaction in this Reactor, non-condensible gases are vented. Then there is withdrawn by flash evaporation and cooling of the residual liquid any amount of excess heat if such there be, as relatively high pressure steam. This would be heat as equivalent steam over and above the heat which is necessary for preheating another batch of the same amount of original raw liquid. This new batch must be raised up to the high temperature — or as close to that high temperature as is possible — which is necessary for the particular chemical reaction or physical process. The excess steam withdrawn may be used for power generation or other use either inside the process itself, or quite externally.

In general, if the chemical or physical change accomplished in the reactor is exothermic, e.g. by a wet combustion, there may be considerably more heat of reaction evolved than that lost in the heat interchanging process in heating up the cold feed liquor by the flash evaporation of the hot liquor in its cooling. Such excess heat may be withdrawn from the process at or near its highest temperature for other utilization, conveniently in the form of steam generated by a flash evaporation of part of the reaction liquors.

Consider also that there is a number, at least 2 or 3, in this case 5 other vessels each of practically identical construction as that of the Reactor vessel, and each with a charge of liquid at temperatures ranging from the lowest up to almost the highest, i.e., that necessary for the reaction to take place by the contacting with some other added material or materials. These may be called the heat transfer vessels and they accommodate the preheating of the raw liquid which otherwise would be done by an ordinary tubular heat exchanger. They may be considered as numbered from the one containing the batch of liquid of the highest temperature as I, II, III, IV and V, with V being originally charged with the raw liquid to be processed at its original, low temperature. V first must be evacuated of non-condensible gases.

Now the hot and pressurized liquid contained in the Reactor, has been heated to the high temperature of the reaction which takes place due to contacting due to the presence of one or more added materials, and has been vented, and has had any excess heat withdrawn as steam from a high pressure flash evaporation as above. This hot liquid is allowed to flash evaporate, with the steam generated thereby being passed, e.g. by a sparger, to condense by open and direct contact with the liquid in Vessel I of highest temperature; and this liquid in I will be heated by this condensation. When a reasonable approach is reached between the temperature in the Reactor and that in the Vessel I, the flash steam valve between the Reactor and I is closed, and the flash steam valve between the Reactor and Vessel II is opened.

Since II is at a lower temperature and pressure then even the lowered temperature and pressure now in the Reactor, flash evaporation again takes place in the Reactor; and the steam formed passes to II to contact the liquid therein and to condense in and heat the contents of II as close as possible to the still further lowered temperature of the Reactor.

This process is repeated with the contents of each successive heat transfer vessel being heated by the steam of progressively lower temperature generated in the Reactor. Finally, the spent liquid in the Reactor will be cooled to a temperature just above that of the liquid in V. This liquid had been raw cold liquid charged into V, but it is now at some higher temperature due to the condensation of steam from the last flash evaporation in the Reactor. The cooled, spent liquid in the Reactor is then discharged, with the desired substantial change in at least one component - the reason for the process as a whole. The former reaction vessel is now charged with cold liquid; and, for a new cycle, it becomes the last stage vessel of the condensation or heat transfer process.

Vessel I now becomes the Reactor for the new cycle. The liquid therein may be heated to the desired temperature for the reaction. Prime Heat may be supplied as may be necessary; e.g. by sparging in live steam of suitable pressure. The reaction then proceeds due to the added other material or materials. In the case of wet combustion, no added heat may be necessary; and a measured amount of oxygen or air is passed in through the sparger at a pressure somewhat higher than that of the liquid. At the critical temperature necessarily attained, either with or without added prime heat, wet combustion takes place to oxidize substantially all or any desired part of the organic materials in the aqueous solution and/or slurry.

This wet combustion may be controlled readily by the rate of the careful metering in of oxygen, air, or a mixture, preferably in small bubbles through a sparger. The large mass of water present compared to the mass of the relatively dilute organic materials greatly dampens the temperature rise as its great specific heat absorbs much of the heat of the combustion. Nevertheless, the pressure and temperature increase markedly — while the rate of their increase is carefully controlled, as also explained in U.S. Pat. No. 3,692.634. At the desired point in the reaction if only a partial combustion is desired or after its completion, non-condensible gases are vented and any product steam is withdrawn.

The added materials - other than oxygen or air for a wet combustion — are usually other liquids or aqueous solutions of solids. They may be added most conveniently usually to the raw original liquid, or if their addition is desired at some other point (e.g. in the Reactor) provision is made for such addition.

The cyclic process is repeated with the hot liquid after the reaction flashing to heat in turn each of the successively colder liquid batches in each of the 5 heat transfer vessels.

For each cycle, the liquid in what had been the Reactor, which had been cooled by the five successive flash evaporations - and reduced somewhat in volume thereby, is drained from the system; and the empty vessel is filled with a new batch of the original liquid, usually at ambient pressure and the lowest temperature. The newly charged contents of the former Reactor now becomes the highest number in the sequence of charges (i.e. the last) which are heated by the steam from the successive flash evaporations in the new reactor. Also each successive vessel now assumes one lower number for the next operation of the cycle.

The pressurizing of the liquid at each stage of the process has been accomplished by the heating of the liquid in the closed vessels due to the condensing of vapors of higher pressure; and from there up to the maximum pressure of the Reactor by the thermal energy (and hence pressure) generated by the wet combustion. (In other cases, the addition of prime heat, e.g. live steam would raise the pressure as well as the temperature.) Thus no pump is necessary except possibly a simple charge pump to fill the empty vessel — the drained Reactor - which may be open to the atmosphere while filling, and before it goes onstream. This charge of original liquid is then heated by the steam from the last flash evaporation, accomplished in the Reactor, the one giving steam of lowest temperature.

In this Sequence A, liquid is charged into one vessel and is not removed — except some steam therefrom — until a complete cycle is finished; and the particular vessel remains with that batch of liquid throughout all of the pre-heating steps, the reaction step, and the several flash evaporation steps.

As indicated above, one simple system of open condensation may be the use of a sparger to supply steam from the flash evaporations as bubbles in the liquid of the batch in each heat transfer vessel. A very high rate of heat transfer is thus achieved. The same sparger may be used with high pressure prime steam to heat a batch of liquid, after it has been preheated to as high a temperature as possible by the batch heat transfer operation. Also it may be used to sparge in, as bubbles, the air or oxygen used for a wet combustion process when the vessel is used as the Reactor.

This Sequence A operates similarly with the use of a closed heat transfer surface, e.g. a tubular heater in each heat transfer vessel rather than the sparging in of the steam from the flash evaporations. The condensate formed from the steam will then be trapped off as distilled water according to standard practice; and there will be a corresponding increase in the concentration of the liquid at the time of the reaction since it has not been diluted by the condensation of steam from the several flash evaporations, also in the concentration of the spent liquid.

Particularly, this Sequence A has the advantage that solids or semisolids may be readily processed in the liquid even though they cannot be pumped or otherwise passed through a pipe line. Thus each vessel would be provided with a suitable opening for charging of the non-pumpable material, e.g. peat as received from the bog with 70–95% water. As the steam from the flash evaporations heats the peat in the heat transfer vessel, it becomes a liquid with solids, some small amount dissolved, but mainly suspended; and finally, after a partial wet combustion it becomes a slurry of solid particles in water which is readily flowable.

Sequence B.

This pattern of operations allows the advantage of maintaining the Reactor as a fixed vessel throughout all cycles. Thus the Reactor may be especially designed for the function of the chemical reaction or physical operation in question. It is then also maintained substantially at the necessary high temperature, without the heat losses due to the wide range of heating and cooling of Sequence A. After the high temperature reaction the Reactor may be vented of non-condensible gases; and these with more or less steam may be used for developing power in an expansion engine.

Another specially designed vessel, the Evaporator, is required. The hot liquid, after the venting, is forced from the Reactor by the maximum pressure at the high temperature there, to the Evaporator. Only a slight loss in pressure is experienced in this transfer. In the Evaporator vessel the several flash evaporations take place. Each generates steam, the first may give high pressure steam representing excess heat if the process produces such over that required for the preheating operation. Then steam is generated at successively lower temperatures and pressures which is passed in turn to the several heat transfer batch vessels, wherein the process liquid is being heated countercurrently, as in Sequence A. The liquid remaining in the Evaporator after these successive flash evaporations then has been cooled to as low a temperature as possible; and it is discharged from the system, usually with a substantially lesser amount of impurities, or other desired change of concentration of its components, as compared with the original feed liquid. In the treatment of waste liquids as sewage sludge or those from pulping operations the BOD or COD of the spent liquid may be so low that it may be discharged directly to a receiving body of water.

At this point, the end of a cycle, the Reactor now is charged with the liquid in the heat exchange Vessel I of the highest temperature. This can be done by venting the Reactor until its pressure is lower than that in I, after which the liquid valve between I and the Reactor is opened to allow I to empty. Similarly liquid is then charged from II to I, from III to II etc. After the liquid in each higher number vessel is removed to pass to the next lower number, the highest number vessel V is charged with the original cold liquid. Then the new reaction proceeds in the Reactor, and its batch of liquid is passed to the evaporator; the liquid therein is allowed to flash evaporate, as before, first for withdrawal of any excess heat as high pressure steam, then in five successive stages with the steam generated going first to I, then to II, III, IV and V. Heat transfer Vessel V is always the last to receive the vapors, of lowest temperature and pressure, from the Evaporator. The cycle is then repeated.

In Sequence B, the Reactor is a separate vessel, and is maintained always in its very high temperature range, and each of the several heat transfer vessels handles its function in the countercurrent relation previously described. Particularly each vessel except the Evaporator remains in the same general range of pressure and temperature of its particular one of the several sequential flash evaporations; and this may represent a substantial saving of heat as compared to Sequence A, depending on the relative mass and heat capacity of the vessels and their contents. Also some economy in design and construction of the heat transfer and reactor vessels may result from the fact that they can be designed for their particular functions and their individual pressure and temperature range of operation.

As described under Sequence A, the other material or materials whether a liquid or solid added to the raw liquid or to any of the batches in the heat transfer vessels, or an oxygen containing gas may be added in Sequence B in a similar way so as to initiate or complete the physical or chemical process desired.

Also, as indicated above, direct condensation of the steam from the flash evaporations may be used as in the Vapor Reheat process, using spargers or other well known methods of accomplishing such immediate contact of vapor and liquid phases. Alternatively, the steam from the flash evaporations may be condensed on closed heat transfer surfaces, e.g. tubes in the heat transfer vessels to produce distilled water and a more concentrated spent liquid.

FIGURES

These are simply diagrams of the flow patterns of fluids in some of the several possible sequences of operation of the process. They are not to scale, do not show necessarily any spacial relation of the components, and do not represent any particular types of equipment. Those types of equipment which may be used for these several operations are conventional and well known. Thus, for example, while "open condensation" is often an essential part of the process and of the equipment for its operation, no indication need be made as to whether this "open condensation" is accomplished in a bulk vapor phase with open streams, droplets, or films of aqueous liquor of lower temperature than the vapors — or in a bulk liquid phase having a sparger or other device discharging steam in bubbles or open streams into the colder bulk liquid. Either may be used, although for convenience of presentation the steam is indicated as being sparged into and below the surface of the particular batch of liquid.

Also various common accessories such as thermometers, meters, pressure gages etc. which may be needful in the operation, but not in understanding the principles of this discussion, are not included in the drawings. Solid lines indicate pipe connections for liquid, i.e. for charging a batch of original liquid into the system, for discharge therefrom, and for flow of batches of liquids between vessels.

FIG. 2 is a schematic diagram for use according to Sequence B where only a single vessel is always used as the Reactor; and it may then be designed especially for its particular function. The heat transfer vessels may be of the same general design, but each is operated at substantially its own particular pressure and temperature range throughout the entire cycle and thus may be individually designed. Thus there would be a range of different design pressures and temperatures going downwardly from I to V. An additional Evaporator vessel allows the several flash evaporations to be accomplished therein, the first possibly for the withdrawal of excess heat as high pressure steam and each successive one to supply steam to each of the batches of liquid charged to the respective heat transfer vessel. The liquid in the highest temperature vessel is passed to the Reactor at the end of each cycle; and that from each vessel of successively lower temperature is then moved up one stage, the raw, cold liquid then is charged into the lowest temperature vessel.

FLOW SHEET OF FIG. 1

Figure 1:
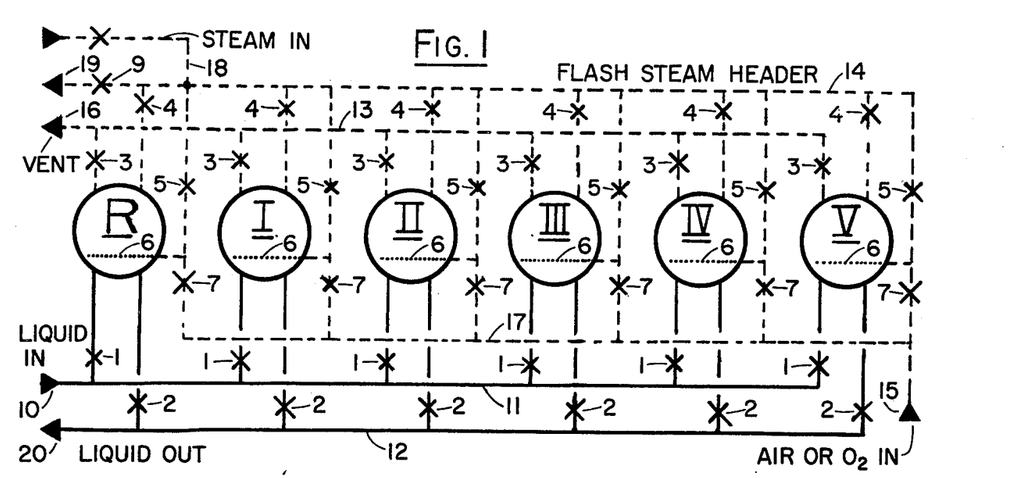
FIG. 1 is a schematic diagram of the arrangement of vessels and piping for use according to Sequence A, with the Reactor and the heat transfer vessels each used for all steps of the process; and therefore all vessels may be assumed as interchangeable and hence substantially identical in design and construction.

FIG. 1 diagrams schematically one embodiment of the method using six vessels which may be substantially the same in design, construction, and interconnecting piping with each other and with outside facilities for supply of original liquid and of added material or materials, also of steam as the source of prime heat, for discharge of spent liquid, and for venting. Of these six vessels, one is being used as the Reactor, the other five are heat transfer vessels. While any larger number than two heat transfer vessels is possible, the larger the number, the more nearly counter current and the more efficient will be the heat transfer operation. Five is chosen here as a useful number for many uses.

FIG. 1 shows the six vessels in a linear arrangement. This may be most convenient for explanation and understanding; but this arrangement is not essential; and an arrangement in a circle may often be simplest and most economical of piping, and also most readily operated. Still other arrangements may have particular advantages in individual cases.

R represents the vessel currently being used as the Reactor, and I, II, III, IV and V represent the heat transfer vessels in decreasing order of temperature and pressure. Valved pipes, 1, at the bottom of each vessel are used to charge the original liquid into the particular vessel from the liquid inlet at 10 via the inlet liquid header 11. For discharging spent liquid, valved pipes 2 are connected from each vessel via the spent liquid header 12 to liquid discharge 20. Valved pipes, 3, at the top of each vessel are used for venting air and other non-condensible gases such as may be present in the original liquid, or as may be formed in the reaction. Such gases discharge via vent header 13 to the vent discharge, 16. Header, 14, is a means for connecting the valved vapor lines, 4, carrying steam generated in flash evaporations from any one vessel to the corresponding valved steam inlet line, 5, connected to any other vessel.

The vessel, wherein the flash evaporation is being conducted, is the Reactor, and each vessel in its turn may be the Reactor. The steam line leaves the top of each vessel, while the connection, 5, to supply the steam to an other vessel is indicated as being made to a pipe, 6, having holes for escape of vapors inside the vessel some distance below the surface of the liquid. Such an inlet pipe for steam in dispersed bubbles is called a "sparger" and the discharge of steam or gas there through is called "sparging". The spargers are indicated by dotted lines.

Thus by opening the valve, 4, on the pipe connected to any vessel of higher pressure the steam generated by flash evaporation of the liquid in this vessel passes through 14 and 5 to the sparger, 6, in the vessel of lower pressure as bubbles to be condensed to heat, as its condensate joins, the liquid therein.

Provision is made for the supply of added material for the reaction in the form of gas, e.g. air or oxygen for a wet combustion, through inlet 15, header 17, and valved lines 7 connected to the respective spargers of the several vessels. If the added material is a liquid or solid dissolved in liquid or a pulverulent solid which can be added in slurry form, it will most easily be added to the raw feed liquid entering at 10 and via 11 through the inlet valve 1 to the particular vessel. Connections could be made to supply such added material separately to any vessel at any stage of the cycle; but since this would not be common, such connections are not shown.

One cycle of the process may be described. After the reaction in the Reactor is completed at the maximum temperature, non-condensible gases may be vented through the valved line 3 connected to the vent header 13 and discharge 16. Also any excess heat may be removed in the form of relatively high pressure steam along with these vented non-condensible gases, or later and separately through valved line, 4, steam exhaust valve, 9, and steam outlet, 19. A flash evaporation in R is then allowed to take place by opening the valve of the vapor line 4 from R to the header 14 and thence opening valve on inlet vapor line 5 to the sparger in vessel I, wherein the pressure and temperature of the liquid are both lower than in R.

The flash evaporation continues in R, as the temperature and pressure therein falls; and the conditions in R soon approach the temperature and pressure in I which have been rising due to the heating by condensation of vapors entering through sparger 6 in I. At this point, the valved line 5 to I is closed; and the valved line 5 to II is opened. A second flash evaporation in R takes place to supply vapors to heat the contents of II almost to the temperature of R — now again lowered.

Similarly other successive flash evaporations are allowed to take place to generate steam to heat the contents of III, IV and V. The last, V, contains the raw liquid feed. The temperature of R each time is reduced by the respective flash evaporation until finally it approaches that to which it has heated the inlet liquor in V. Now, the contents of R is discharged as spent liquid through its valved line, 2, the liquid discharged header, 12, and the liquid discharge, 20. When R is empty, it is filled with raw inlet liquid.

This batch heat exchange operation conducted between the contents of R and that in the respective vessels I–V may not raise the temperature of the liquid in I up to that critical temperature necessary for the desired chemical or physical reaction for the next cycle to take place or even to be initiated. Usually this is because a particular reaction does not give off sufficient heat to preheat the feed liquid and to make up for the net heat loss of the bath heat exchange system. In that case prime heat, as saturated steam at a temperature equal to or slightly greater than that necessary for the reaction to take place or to be initiated, is added from valved steam inlet, 18, steam header, 14, and valved line, 5, to the sparger of the heat transfer vessel which has been heated to the highest temperature in the previous cycle, now I. The reaction now takes place due to the added material or materials — either added at this point or to the original liquid, or to any of vessels during the heat transfer cycle. I now becomes the Reactor R; II becomes I, etc., as each successive vessel assumes one lower number, and the reactor of the previous cycle becomes V as it is charged with raw liquid.

This batch cycle is repeated indefinitely according to the schematic diagram of FIG. 1 which shows the six vessels arranged in a line parallel to the flash steam header 14, the vent header 13, the liquid-out header 12 and the liquid-in header 11. In the following cycle, the reaction takes place in-or the Reactor becomes — the vessel successively taken next to the right. (The vacancy at the far left is taken by the vessel number which is eliminated at the far right.) Similarly the discharge of spent liquid from the Reactor after cooling, and then also the inlet of raw liquid - with or without added material — is successively from or into vessels taken in a progression moving to the right. The temperature and pressure in the vessels increases from right to left with continuity established by vessels dropped at right and added at left.

The operational cycle in each particular vessel starts with its charging with a batch of cold raw liquid. This is heated countercurrently during each of five stages by the condensation of steam from the appropriate flash evaporation of each cycle, then finally with prime heat and/or the heat of the reaction. The particular vessel, having been represented during six cycles as the batch in V, IV, III, II, I, and R, then is cooled, from the maximum temperature of the reaction of its contents by the five successive flash evaporations and is then discharged from the same vessel wherein the entire processing of that batch has taken place. This vessel is then charged with raw cold liquid to begin again the round of cycles.

As noted above, often there is an exothermic reaction, e.g. wet combustion which may heat the batch of liquid in the reactor to a temperature much higher than that necessary for accomplishing the preheating operation in the heat transfer vessels I to V. This excess heat may be readily withdrawn for external power to process use by a first flash evaporation in R immediately after venting non-condensible gases, before or during such venting, or even during the reaction itself. Valve line 4 from R and exit steam valve 9 are opened to allow steam, with or without non-condensible gases to discharge at 19 for other use. The steam with or without non-condensibles is often at a high pressure — 50 to 100 atmospheres pressure, or even more. Flash evaporation then takes place until the liquid in R is cooled to the temperature level at which it can still generate sufficient steam to supply the necessary heat for preheating in turn the batch in each of the heat transfer vessels I to V.

FIG. 1 diagrams schematically not only the use of direct condensation of the open steam generated in the several flash evaporations by the Vapor Reheat system, but also the indirect condensation of closed steam if there be considered a closed, tubular heat transfer system submerged in the liquid in each vessel in place of the indicated sparger 6. Also required then would be a drainage and trap system connected to the tubular heat transfer system to remove the condensate, i.e. distilled water.

Not shown in FIG. 1 are any necessary accessories for charging solids or semi-solids such as peat into each of the vessels. These would be conventional equipment and would be provided, to each of the vessels. Such accessories are indicated schematically in FIG. 1 simply by the entrance for liquid 10, the header 11, and the valved inlet lines 1, nor are means shown for venting non-condensibles to partial vacuums when necessary.

FLOW SHEET OF FIG. 2

Figure 2:
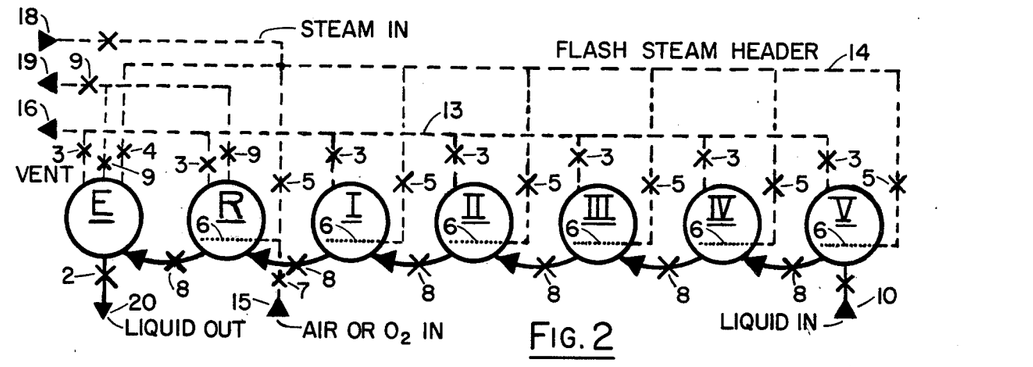

FIG. 2 also uses a Reactor and five vessels for the batch heat transfer operation; but as opposed to FIG. 1, each one always operates in the same temperature and pressure range. There will be less heat lose when operating as in FIG. 2 than that due to the cooling of the vessels themselves in FIG. 1, from the highest temperature of the process to the lowest temperature. Furthermore, since the pressure range may often be considerable, each vessel for the highest pressure may be made of the heaviest material, and vessels for lower pressure of lighter material. This may make a considerable saving of cost of vessels for lower pressures as compared to those of FIG. 1, where all must be built to withstand the highest pressure of the process, i.e. that when it is used as the Reactor.

In the flow sheet of FIG. 1, a single vessel acts as the Reactor in all cycles of the process, thus it also may be designed for the desired maximum pressure and temperature, as well as the other conditions for the reaction operation as distinguished from the simpler conditions required for the condensation of vapors accomplished in the operation of the heat transfer vessels.

An additional vessel is supplied in FIG. 2, an Evaporator, E ; and this also is designed for its special function of accomplishing the series of flash evaporation, the essential half of the batch heat transfer operation in cooling the batch which is at the high temperature after the reaction. There is an important difference in the operation of the process according to FIG. 2, contrasted to that of FIG. 1 wherein no transfer of liquid takes place; and the entire processing of a batch of raw liquid in FIG. 1 takes place without transfer from a single vessel. In FIG. 2 the aqueous liquid is moved, by the pressure generated by the heating actions, sequentially to vessels wherein separately, each of the several steps are accomplished.

Again in FIG. 2 there is shown a linear arrangement of the vessels, although, as in FIG. 1, a circular or other arrangement may have advantages. The order of the vessels and their functions are fixed in FIG. 2, with the liquid of each batch being moved in its position rather than, as in FIG. 1 the vessel is itself being moved in effect in its relation to the others by changes in the valves of the piping.

The reaction is assumed to have taken place in the batch in the Reactor, R, due to added material — gaseous, as an oxygen containing gas from valved pipe 7 for a wet combustion; or solid or liquid added to the original raw liquid or directly to R. Non-condensible gases are vented from R by 3, via 13, to the vent discharge 16. The liquid is now at substantially the highest pressure and temperature which the batch encounters in the system; and it is forced from R through valved line 8 to the empty E which may be slightly vented if necessary at the start of the transfer operation through its vent valve 3. A flash evaporation of the batch now in E generates high pressure steam for other process or power use. This steam is withdrawn through valve 9 and outlet 19 in as large an amount as possible without cooling liquid in E so much that it cannot supply adequate heat for the subsequent heat transfer operation of preheating raw liquid.

The several vessels, I to V, are assumed to be filled with batches of raw liquid of successively lower temperatures; and V contains the original cold liquid.

Next is a succession of five flash evaporations in cooling the liquid in E. The flash steam valved line 4 of E is opened to header 14; and for the first flash evaporation valve 5 to sparger 6 of I is opened to allow steam from the higher pressure of E to flow into the lower pressure of I as bubbles from sparger 6. This steam is condensed, and heats the batch of liquid in I. When the temperature in I is almost that of the now reduced temperature in E, valve 5 to I is closed; and valve 5 to the sparger in II is opened. The operation is repeated, thereby heating liquid in II. Similarly the liquid in each of III, IV and V is heated, while correspondingly the liquid in E is cooled. When liquid in E is at a temperature approaching that in the now somewhat preheated, but originally cold, liquid in V, the operation is stopped; and the spent liquid in E is discharged from valve line 2 to pass out of the system at 20.

Either after the succession of batch heat transfer operations or while they are in progress, the preheated liquid in each of the several heat transfer vessels may be transferred one vessel to the left to the next higher temperature stage of the next lower number. Thus vent valve 3 or R — which is empty — is opened slightly until the pressure therein is less than that in I; then valved line 8 between I and R is opened to allow the greater pressure in I to force its liquid into R, and valved line 8 between R and I is then closed. Next, vent valve 3 of I is opened until pressure in I is less than in II; and valved line 8 between I and II is opened to allow the greater pressure in II to force its batch of liquid into I. This operation is repeated for III, IV, and V; and when V is emptied, it is filled with cold raw liquid.

The cycle is now complete; and it may be repeated indefinitely.

Again, FIG. 2 may also be considered not only as a schematic of the process of heating of the feed liquid in batches by open condensation in the heat transfer vessels of liquid by steam from flash evaporations in E; but also as a schematic for the indirect heating through closed condensation on heat transfer surfaces in each of I, II, III, IV, and V. If 6 in each of the vessels is considered to represent not a sparger but instead a tubular heater; and if there is connected to each, a suitable trap for removal of condensate, the flow sheet diagrams the features of indirect condensation, i.e. production of distilled water, higher concentration of spent liquid, also the higher costs due to the heat transfer surfaces.

CHEMICAL REACTIONS IN LIQUIDS AT ELEVATED TEMPERATURES

This invention comprehends the batch heating and cooling of aqueous solutions, suspensions, or slurries with a reaction accomplished during or after the heating to the highest temperature and before the cooling of a particular batch. The several processes which are improved when so operated include many types of partial or almost complete wet combustions of organic materials contained in dilute solutions, with or without substantial amounts of inorganic matter, suspensions of particulate matter, or slurries of fines including matter with colloidal properties.

Wet combustion of a particle or even of a complex organic molecule does not take place in a single reaction or flame or flash, as might be considered for the burning of a drop of benzene or a small bit of paper suspended in oxygen. In wet combustion there may be many steps in the breakdown of molecular structures resulting in their more or less complete combustion at the high temperatures of the reaction in the presence of water and oxygen. Intermediate compounds of the reactions may be oxidized further to a greater or less extent, i.e. they may vary from "soft" to "hard" compounds depending on the relative ease of oxidation.

This compares with the usual burning of benzene in air, where the black smoke usually produced indicates "hard" compounds, highly carbonaceous material very much more difficult to burn than the hydrogen containing compounds first cracked or burned out of the benzene ring. Also the molecules in a single sheet of newspaper, as it burns in air, decompose and combust to give various intermediate compounds on the chemical path ultimately to $CO_2$ and water. These intermediates may also vary greatly as to their ease of further oxidation; and always the burning of a single sheet of paper in air leaves a thin black shell of carbonaceous material, because the temperature of the instant flame formed by burning the soft compounds is not high enough for complete combustion of the harder compounds, The stages of wet combustion may be much more numerous and are much more readily controlled; and they may be stopped almost at will by the control of conditions.

The time of the combustion or of the desired partial combustion reaction itself will depend on many factors, among others: the temperature, the partial pressure of the oxygen present - hence its activity as controlled by the extent of its dilution with nitrogen from the air and $CO_2$ from the reaction, possibly some catalytic effect of other materials present, also the dilution of the organics, i.e. the amount of water present, which is usually 5 to 20 times that of the organics. In general, the time required for the reaction may vary from one minute to 200 minutes, as the time that the liquid and added material or materials are maintained in contact in the reaction temperature range, which usually may be at any temperature above 300° to 400° F. Thus the reactor will be designed according to the particular reaction and its critical or controlling conditions.

Most wet combustion processes supply adequate heat in the form of steam generated by the several flash evaporations of the hot liquid and condensed to the heat exchanging vessels to preheat subsequent batches for the reaction. Each batch must be raised to the critical temperature, usually 275° –400° F, necessary for the initiation or continuance of the reaction. Usually there will be some excess heat available; i.e. the reaction liquors will be raised to a higher temperature than necessary. This excess heat may be withdrawn in steam of relatively high pressure and usually with non-condensible gases contained therein — 500 to 3000 pounds per square inch at 500°–700° F — or at a considerably lower pressure with very much less non-condensibles if pure oxygen is used for the combustion. By first withdrawal of non-condensibles with some steam, and then flash evaporating the liquid, there is generated steam which is almost free of non-condensible gas and may be used for power or other process use. In other cases the steam mixed with non-condensibles may be used equally well, particularly for power generation in an expansion engine.

If the reaction is endothermic, or insufficiently exothermic, e.g. if less than 1% organics is present, prime heat will be required. This may be supplied in any one of several ways, including sparging live steam directly to the reactor, or it may be by addition of an organic liquid or solid to the raw liquid as fuel for a wet combustion, or it may be by submerged combustion of a fluid fuel.

Many materials among which are carbohydrates (sugars, starches, celluloses) will be partially hydrolyzed during the preheating process, and their hydrolyzates and many other complex organic molecules will decompose and oxidize in several steps under the conditions before ending up as $CO_2$ and water. This hydrolysis during the preheating may be accelerated by the addition of sulfuric acid, usually an amount of less than 1%, to the raw liquid. This acid may be neutralized if desired in the reactor before the wet combustion.

Particularly is this hydrolysis noticeable with the very large molecules of colloids and polymers. Thus the gummy and colloidal materials which retain water and make up the structure of peat are probably hydrolyzed during the preheating so that they are then readily partially oxidized utilizing only a small amount of the available heating value of the peat in breaking its amorphous mass into granular, readily filterable and dried, solid particles.

Thus, the hydrolysis of organic molecules may be an important factor in their decomposition into smaller molecules, and the subsequent partial or complete wet combustion of these smaller molecules formed. Particularly in the batch operation of this invention, time and opportunity for such hydrolysis are allowed in the several heat transfer vessels; and the resulting hydrolyzates may be much more readily combusted somewhat later in the reactor.

The wet combustion may yield products of commercial value at different steps in its completion of the partial oxidization. One of these is acetic acid, often a result of oxidation of organic molecules — biochemically or otherwise. In the presence of an alkali — as that present in many waste liquors of the wood pulping industry, or separately added, the soluble acetate salt is formed. This also may be further oxidized although with somewhat greater difficulty; but if the wet combustion is controlled properly as to time, temperature, and concentration of oxygen, the spent liquor discharged may retain an optimum amount of acetate salt. This acetate salt may be treated with sulfuric acid or a sulfur oxide to give acetic acid, which is extracted from the liquor, and then recovered as pure acetic acid by known means, e.g. U.S. Pat. No. 2,878,283. The resulting liquor with important soda and sulfur values, may be worked up for reuse, particularly in the kraft pulping process.

The hydrolysis of cellulose, from wood or other lignocellulose fibers, sawdust, chips or other particles may be accomplished by the batch heating, reaction, and cooling of the lignocellulose material in an aqueous liquid by the process of this invention. Some prime heat is required over that produced in the reaction. 8 to 10 times as much dilute sulfuric acid of 0.5 to 3.0% strength has been used to make a slurry of hardwood sawdust with a reaction time of 2 to 15 minutes at temperatures of 300° to 375° F. From 60 to 90% of the cellulose was hydrolyzed to water soluble materials which, based on the original dry sawdust, gave yields of 3 to 4% furfural, 4 to 7% organic acids, — principally acetic, and 20 to 25% reducing sugars, which may be used for fermentation to alcohol or other products. The residue largerly ligninwith unreacted cellulose, was from 30% to 60% of the weight of the original sawdust on a dry basis and varies inversely as the percent of hydrolysis. The lignin is readily filtered from the cooled spent liquid and was readily dissolved by a solvent from the residue for use as an extender in elastomers and thermosetting resins.

The hydrolysis liquid, after removal of the lignin, may also be worked up by conventional process for the recovery of its content of acetic acid and furfural. Either with or without these volatile liquids, the reducing sugars of the liquid may be partially oxidized in a following or separate wet combustion to give acetic acid, or an acetate salt, as above described.

Using a partial combustion by the process of this invention, and by probably some of the same chemical reactions as occur later in the conversion to acetic acid of carbohydrates, such as these reducing sugars, cellulose, or others, ethyl alcohol in solution in the raw liquid has been found to be partially oxidized, to acetic acid — or in presence of an alkali to the alkali acetate. Again, the acetic acid may be recovered from the spent liquids by conventional processing.

Similarly, and by the use of the processing of this invention with the different standard cooking liquors associated with different conventional wood pulping processes, wood particles or chips as in the original liquid, and preheated, react to be delignified to give cellulose and the conventional black liquors associated with each pulping process. Cooling will be by the multiple flash evaporations. Additional heat will be required — most conveniently as prime steam; but considerable heat is saved by this heat recovery system compared to conventional pulping operations.

Black liquors from pulping operations, and others of low value containing waste organics may be processed by this batch wet combustion in the presence of added materials, such as oxides, hydroxides and, less desirably, carbonates of metals as calcium, magnesium and iron. These basic metallic compounds may be in crude form, even as mined ores after being pulverized. Under the conditions of a partial wet combustion itself, or during the cooling of the liquors therefrom, the metals themselves form complexes with some of the organic molecular species present which are quite insoluble; and these complexes may be separated from the spent liquid by filtration to give cheap but useful fillers for asphaltic materials used in road and similar construction.

With the control of temperatures, time, and oxygen supply of the wet combustion process, many organic materials in pulverulent or granular form may be carbonized; i.e the more readily oxidized parts of the molecular structure are reacted leaving a highly carbonaceous residue. Control of the combustion to remove all but the most recalcitrant residue gives a carbon of greater or less activity as an absorbent. Similarly, granular or pulverulent activated carbons when charged with adsorbed organic materials may be reactivated by a controlled partial wet combustion which will oxidize off the absorbed organic materials and leave the much less combustible carbon with its "sites" for adsorption cleaned or reactivated for reuse. With water carbons, i.e. those used to purify aqueous solutions, such wet combustion reactivation saves most of the considerable processing cost of removal of the spent wet carbon from its bed, drying and burning off the adsorbed organics at a high temperature using highly superheated steam, then cooling and transferring back to the original bed. Heat costs and transfer costs are high for the conventional high temperature process particularly when the capital charges of the considerable amount of equipment are included. The present process handling the wet carbon always in a slurry is very much less expensive.

As noted above, this batch process may be particularly advantageous when smaller amounts of liquid are to be reacted. Liquids resulting from processing of silver halide coated photographic films and paper contain much silver, and especially when the emulsions of waste photographic films and papers are removed. also considerable organics, including colloidal material from the emulsions. Usually these liquids are concentrated to a sludge which is burned to recover the silver; and this system has attendant losses in obtaining the residue from the furnace and from the stack gases. Alternatively this batch wet combustion process allows the removal, in the spent liquid, of a residue with a very high content of metallic silver obtained either from the liquids from photo processing themselves or from the sludge therefrom. Particularly if there is used the open condensation of the steam generated in the flash evaporations, there is very little loss by entrainment of silver in the steam. Almost 100% of the silver in the raw liquid or sludge may be recovered by decanting off or filtering off the spent liquid from the black residue, which then is washed, and worked up by conventional processing to obtain silver bullion. Similarly, silver may be recovered from waste films and papers which have been ground and pulped in water.

This batch wet combustion process provides a sure method of burning and thus destroying organic materials due to:

(a) the excellent control of the rate of burning through the control of the rate of adding oxygen and/or air, (b) the large amount of water present which is a very effective reservoir of heat and prevents a too rapid rise of temperature, and (c) the possibility of simultaneously venting and flash evaporation to hold down the temperature.

Thus materials which burn violently or explode in air may be safely wet combusted, for example: waste nitrocellulose, gun powder and other explosives which must be destroyed because they are older than their expected safe life, or for other reasons. The wet combustion either may be complete or carried only to quite innocuous intermediary compounds.

PHYSICAL OPERATIONS WITH LIQUIDS AT HIGH TEMPERATURE

There are many physical treatments of liquids which are best done at temperatures elevated from the ambient. Here again, the heat transfer system of the present invention in heating batches of the raw liquor from ambient temperature to the higher temperature and then cooling them to the lower temperature may represent a substantial saving in heat. As with chemical reactions at an elevated temperature, the steam from the flash evaporations may be condensed directly by open contact with the raw liquid being preheated in the respective heat transfer vessels, or the steam may be condensed in tubular heaters in the vessels to give separate condensate, as distilled water, and a more concentrated spent liquid than the raw liquid.

One example of a physical operation which is improved by the application of the process of this invention is the desalination of sea water by the use of solvents as described in U.S. Pat. No. 3,692,634 which have not significant solubility for the salt in sea water but do have a greater solubility for water at an elevated temperature than at the ambient temperature.

Thus, after having any necessary prime heat added, the sea water is contacted with a solvent of this class in the Reactor which in this case might be in the form of a liquid-liquid extractor. The solvent dissolves a significant amount of water away from the sea water; and, if now the solvent is cooled by heat exchanging, this water may be decanted out, and the more concentrated sea water is subjected to the multiple flash evaporations to cool it and generate steam for preheating the raw sea water. The preheating is done by closed condensation, so that this condensate as well as the pure water extracted at the high temperature is the product, desalinated water, at a low heat cost compared to conventional processing.

I claim

1. In a process of heating, reacting with an added material, flash evaporating, and condensing vapors so formed of individual batches of an original aqueous liquid wherein there is no mechanical pumping of said liquid during the processing cycle, the steps comprising:
    a. arranging in the order of decreasing temperature a series of batches of said original aqueous liquor, each batch being preheated in one of a series of heat transfer vessels;
    b. supplying heat to heat further at least a major part of the batch of said liquid of the heat transfer vessel which has been preheated to highest temperature, so that this batch is raised to an even higher temperature, the maximum temperature in the process, and said batch becomes the hottest batch of liquid in the process;
    c. contacting said hottest batch with an added material which at said maximum temperature changes the concentration of at least some of the components of the liquid in said hottest batch;
    d. subjecting said hottest batch of liquid, with the concentration of at least some of its components changed, successively to a series of as many individual and separate flash evaporations as there are heat transfer vessels exclusive of the vessel containing said hottest liquid, the first of which individual flash evaporations generates an amount of steam at the highest temperature of any of said flash evaporations; and each successive flash evaporation generates an amount of steam of a successively lower temperature;
    e. condensing said amount of steam of highest temperature which is generated by said flash evaporation in the condensing zone of the heat transfer vessel of the next highest temperature below said maximum temperature so as to preheat the batch of liquid therein, and condensing said steam generated in each successive flash evaporation at each successively lower temperature in the condensing zone of the heat transfer vessel taken serially in the order of successively lower temperatures, until the steam generated at the lowest temperature condenses to preheat the batch of raw original liquid which is at the lowest temperature of the process;
    f. cooling by each of said individual flash evaporation said liquid of what had been the hottest batch, so that after each of said flash evaporations, its temperature approaches the temperature of the liquid of the batch in the heat transfer vessel wherein was condensed the steam of this particular flash evaporation; and
    g. continuing said cooling of said liquid of what had been the hottest batch until its temperature approaches that of the batch of lowest temperature which was the one last charged with the original liquid.

2. In a process according to claim 1 wherein the steam generated by each of said flash evaporations is directed in open, dispersed flow, and in direct contact with the liquid of the respective batch in the condensing zone of the particular one of said heat transfer vessels; and the condensate so formed mixes with said respective batch of liquid.

3. In a processing according to claim 2 wherein the steam from each of said flash evaporations is sparged beneath the surface of the corresponding batch of liquid in the respective heat transfer vessel, said steam being in the form of bubbles which condense in said batch of liquid.

4. In a process according to claim 1 wherein the steam from each of said flash evaporations is condensed on a closed heat transfer surface in the condensing zone of the particular one of said heat transfer vessels; and the condensate is withdrawn separately and is unmixed with the respective batch of liquid which is heated by said condensation.

5. In a process according to claim 1 wherein said original aqueous liquid contains oxidizable organic matter and said contacting with an added material comprises addng oxygen to cause wet combustion of at least part of the oxidizable organic matter contained in the original aqueous liquid, whereby carbon compounds containing a greater amount of oxygen are formed of said organic matter.

6. In a process accordin to claim 5 wherein said oxidizable organic matter contains sewage waste.

7. In a process according to claim 5 wherein said oxidizable organic matter is contained in peat.

8. In a process according to claim 5 wherein said oxidizable organic matter is in an aqueous suspension-solution which has been derived from the pulping of ligno-cellulosic material in giving cellulose and lignin related compounds.

9. In a process according to claim 5 wherein said wet combustion is controlled to produce solids which have a higher percentage of fixed carbon than that of the said oxidizable organic matter.

10. In a process according to claim 9 wherein said solids produced have a substantial activity in adsorbing other chemical compounds.

11. In a process according to claim 1 wherein said original liquid contains particulate solids which when activated adsorb organic material and said contacting comprises adding oxygen to said activated particulate solids while carried in said original liquid, said particulate solids containing oxidizable organic material adsorbed thereon; so as to produce a controlled wet combustion of the adsorbed oxidizable organic material but not of said particulate solids, thereby reactivating said particulate solids so that they will again adsorb organic material.

12. In a process according to claim 11 wherein the particulate material is an activated carbon.

13. In a process according to claim 1 wherein said batch of liquid raised to said maximum temperature is maintained at a temperature higher than that in any of said heat transfer vessels for a period of from 1 to 200 minutes.

14. In a process according to claim 1 wherein said process is conducted in succession of cycles, each cycle comprising:
  a. preheating an individual batch of liquid by condensing amounts of steam generated in flash evaporations of previous batches, the last amount of such steam coming from the next preceding batch;
  b. further heating said batch to a still higher temperature which is the maximum in the process;
  c. contacting said batch with an added material which at said maximum temperature causes a change in the concentration of at least one of its components;
  d. flash evaporating said batch so as to generate a series of amounts of steam while cooling said batch to a final temperature approaching that of the orginal liquid;
  e. directing each of said series of amounts of steam serially to said heat transfer vessels in the order of from the one of highest temperature to the one of lowest temperature, said heat transfer vessels being charged with subsequent batches of liquid taken serially in the heat transfer vessels after said batch in the order of from the one with the highest temperature to the one with the lowest temperature;
  f. condensing each of said amounts of steam generated in one of said multiple flash evaporations to its respective batch in said series of heat transfer vessels, thereby preheating subsequent batches countercurrently to said cooling of said batch;
  g. discharging said batch from the system after it has been cooled to a temperature approaching that of the original liquid; and
  h. charging a new batch of original liquid into the heat transfer vessel which has become the one of lowest temperature.

15. In a cyclic process according to claim 14 wherein said individual batch of said liquid remains in a single vessel throughout all of said processing steps.

16. In a process of claim 14 wherein said individual batch of said liquid is moved through each of a sequence of heat transfer vessels from the one of lowest temperature wherein it is charged into the system to the one of highest temperature, then through a reactor, then finally through an evaporator and the discharge from the system.

17. In a process according to claim 16 wherein said movement of said individual batch of liquid to each of said sequence of heat transfer vessels after the one of lowest temperature to which it is charged, to said reactor, and to said evaporator is accomplished by first venting to a lower pressure than that of said individual batch the empty vessel to which it is to be moved, and forcing said batch of liquid from the vessel it has been occupying to the one to which it is to be moved by the pressure of the steam in equilibrium with said liquid in said occupied vessel.

18. In a cyclic process according to claim 14 wherein the steam generated by each of said flash evaporations is directed in open and dispersed flow and in direct contact with the liquid of the respective batch which is in the condensing zone of the particular one of said heat transfer vessels; and the condensate so formed mixes with said respective batch of liquid.

19. In a process according to claim 14 wherein the steam from each of said flash evaporators is condensed on a closed heat transfer surface in the particular one of said heat transfer vessels; and the condensate so formed in withdrawn separately and is unmixed with the respective batch of liquid which is heated by said condensation.

20. In a process according to claim 5 wherein the heat required to raise the temperature of a batch of liquid from that of the heat transfer vessel of highest temperature to that of the maximum temperature in the process is supplies by said wet combustion.

21. In a process according to claim 20 wherein an excess of heat is produced by said wet combustion over that which is required to raise the temperature of a batch of liquid to said maximum temperature in the process and to supply heat for said preheating in said heat transfer vessels.

22. In a process according to claim 21 wherein said excess heat is used in raising the temperature of said hottest batch; and at least a part of said excess heat is removed by cooling said hottest batch from said highest temperature by a flash evaporation prior to those flash evaporations used to generate those amounts of steam which preheat subsequent batches; and the steam generated by said prior flash evaporation is withdrawn for use outside of the process at a temperature higher than that of any of the amounts of steam generated to preheat subsequent batches.

23. In a process according to claim 22 wherein at least a part of the steam generated in removing said excess heat contains a substantial amount of the gaseous products of said wet combustion.

24. In a process according to claim 14 wherein said original liquid contains carbohydrate material and said contacting of said liquid with an added material comprises adding sulfuric acid in a concentration of 0.1 to 3% of the water content whereby said carbohydrate material is hydrolyzed.

25. In a process according to claim 24 wherein the carbohydrate is that in lignocellulose materials.

26. In a process according to claim 25 wherein the hydrolyzates include reducing sugars, furfural, and acetic acid with a residue containing much of the liqnin present in said original ligno cellulosic materials.

27. In a process according to claim 14 wherein said original liquid contains wood particles; and said contacting with an added material comprises adding of chemicals conventionally used in aqueous solution for pulping of wood, whereby the cellulose in said lignocellulose material is delignified to a major extent.

28. In a process according to claim 5 wherein said wet combustion is only partially complete; and acetic acid is formed as an intermediary product of said partially complete wet combustion.

29. In a process according to claim 28 wherein a soluble alkali is an added material to react with said acetic acid.

30. In a process according to claim 5 wherein said oxidizable material may be those in the spent liquors from the hydrolysis of ligno cellulosic materials including a hydrolyzate of water soluble wood sugars, furfural, and acetic acid with an insoluble residue containing much of the lignin present in said original ligno-cellulosic material, said wet combustion being only partially complete, so as to increase the amount of acetic acid in the spent liquors.

31. In a process according to claim 30 wherein said residue of lignin is separated from said liquors resulting from the hydrolysis of ligno-cellulose materials before said wet combustion, said wet combustion is only partially completed, so as to increase the amount of acetic acid in the resulting spent liquid.

32. In a process according to claim 55 wherein said web combustion is only partially complete, said oxidizable organic matter includes an aliphatic alcohol, said alcohol being oxidized to the corresponding acid which is obtained from the spent liquors.

33. In a process according to claim 32 wherein said alcohol is ethanol, and said corresponding acid is acetic acid.

34. In a process according to claim 8 wherein said wet combustion is only partial, and an oxide of a metal selected from a class consisting of calcium, magnesium, and iron is an added material, whereby an insoluble complex is formed with said lignin related compounds.

35. In a process according to claim 8 wherein said wet combustion is only partial, and a hydroxide of a metal selected from a class consisting of calcium, magnesium, and iron is an added material, whereby an insoluble complex is formed with said lignin related compounds.

36. In a process according to claim 5 wherein said oxidizable organic matter contains colloidal and other organic materials and silver compounds derived from processing photographic films and papers, said organic materials being substantially destroyed by said wet combustion to give in the spent liquid a concentrated and readily separable sludge containing at least most of the silver values.

37. In a process according to claim 5 wherein said oxidizable organic matter comprises waste explosives which are safely destroyed by at least a partial wet combustion.

38. In a process to claim 1 wherein said original aqueous liquid is sea water; and said contacting with an added material comprises the addition of a solvent which has substantially no solubility for the salt in said sea water and a greater solubility for water at said maximum temperature than at lower temperatures, separating and cooling to a lower temperature said solvent charged with water, now desalinated, whereupon a part of said desalinated water comes out of its solution with said solvent at said lower temperature, and decanting from said solvent at said lower temperature said part of said desalinated water which has come out of solution.

39. In a process according to claim 14 wherein said individual batch has been preheated by condensing of said amounts of steam generated by said multiple flash evaporations from at least two of the prior batches.

40. In a process according to claim 1 wherein said heat transfer vessels are arranged substantially on a circle.

* * * * *